(12) United States Patent
Hayano et al.

(10) Patent No.: US 9,469,612 B2
(45) Date of Patent: *Oct. 18, 2016

(54) POLYETHER COMPOUND AND ELECTROLYTE COMPOSITION

(75) Inventors: Shigetaka Hayano, Tokyo (JP); Yasuo Tsunogae, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 8 days.

This patent is subject to a terminal disclaimer.

(21) Appl. No.: 14/008,283

(22) PCT Filed: Mar. 30, 2012

(86) PCT No.: PCT/JP2012/058585
§ 371 (c)(1),
(2), (4) Date: Sep. 27, 2013

(87) PCT Pub. No.: WO2012/133769
PCT Pub. Date: Oct. 4, 2012

(65) Prior Publication Data
US 2014/0012012 A1    Jan. 9, 2014

(30) Foreign Application Priority Data

Mar. 31, 2011    (JP) ................................. 2011-081298

(51) Int. Cl.
| C07D 233/64 | (2006.01) |
| C08G 65/24 | (2006.01) |
| C08L 71/03 | (2006.01) |
| C08G 65/333 | (2006.01) |
| H01B 1/12 | (2006.01) |
| C08G 65/10 | (2006.01) |
| C08G 65/26 | (2006.01) |

(52) U.S. Cl.
CPC ........... *C07D 233/64* (2013.01); *C08G 65/105* (2013.01); *C08G 65/24* (2013.01); *C08G 65/2654* (2013.01); *C08G 65/33317* (2013.01); *C08L 71/03* (2013.01); *H01B 1/122* (2013.01)

(58) Field of Classification Search
CPC  C07D 233/64; C07D 231/12; C07D 249/08; C07D 233/56; A61K 51/0478
USPC ...................................................... 548/341.1
See application file for complete search history.

(56) References Cited

U.S. PATENT DOCUMENTS

| 6,376,765 | B1 | 4/2002 | Wariishi et al. |
| 2006/0047054 | A1* | 3/2006 | Wang ........................ C08F 8/30 524/495 |

| 2006/0076051 | A1 | 4/2006 | Watanabe et al. |
| 2010/0319762 | A1 | 12/2010 | Watanabe et al. |
| 2010/0326500 | A1 | 12/2010 | Watanabe et al. |
| 2013/0214209 | A1 | 8/2013 | Hayano et al. |

FOREIGN PATENT DOCUMENTS

| JP | 9-201539 A | 8/1997 |
| JP | 2001-256828 A | 9/2001 |
| JP | 2002-246066 A | 8/2002 |
| JP | 2004-35868 A | 2/2004 |
| JP | 2004035868 A * | 2/2004 |
| JP | 2004-217565 A | 8/2004 |
| JP | 2010-53217 A | 3/2010 |
| JP | 2010053217 A * | 3/2010 |
| WO | WO 2004/112184 A1 | 12/2004 |
| WO | WO 2012/057299 A1 | 5/2012 |

OTHER PUBLICATIONS

International Search Report for PCT/JP2012/058585 mailed on Jun. 12, 2012.
Extended European Search Report dated Apr. 30, 2015, issued in corresponding European Patent Application No. 12764210.6.

\* cited by examiner

*Primary Examiner* — Alicia L Otton
*Assistant Examiner* — Sagar Patel
(74) *Attorney, Agent, or Firm* — Birch, Stewart, Kolasch & Birch, LLP

(57) ABSTRACT

A polyether compound containing oxirane monomer units in an average number per molecule of 10 to 100, wherein the polyether compound contains repeating units which are represented by the general formula (2) as at least part of the oxirane monomer units is provided. According to the present invention, it is possible to provide a polymer material which has suitable fluidity and is excellent in ion conductivity.

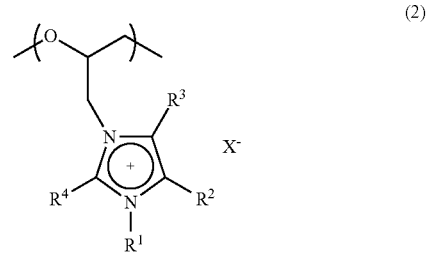

(2)

($R^1$ to $R^4$ respectively independently indicate a hydrogen atom or $C_1$ to $C_3$ alkyl group, and $R^2$ and $R^3$ may be bonded with each other. Further, $X^-$ is an anion which is comprised of 2 to 25 atoms.)

6 Claims, No Drawings

POLYETHER COMPOUND AND ELECTROLYTE COMPOSITION

TECHNICAL FIELD

The present invention relates to a polyether compound and an electrolyte composition which contains the same, more particularly relates to a polyether compound which is excellent in ion conductivity and which has suitable fluidity, so can be suitably used as a polymer electrolyte.

BACKGROUND ART

In the past, to obtain ion conduction between electrodes in secondary cells, fuel cells, dye sensitized solar cells, actuators, and other electrochemical devices, a liquid electrolyte comprised of an electrolytic salt dissolved in a solvent has been used. However, with a liquid electrolyte using a solvent, reduction in the amount of liquid along with time due to evaporation of the solvent or liquid leakage is liable to occur, so development of an alternative electrolyte has been studied.

As an alternative electrolyte to a liquid electrolyte using a solvent, utilization of a nonvolatile ionic liquid has been studied. For example, Patent Document 1 proposes an electrolyte composition which contains an imidazolium compound or a pyridinium compound which has an oligoether group as a substituent. By using such an ionic liquid as an electrolyte, the problem of the reduction in the amount of liquid along with time due to evaporation of the solvent or liquid leakage which is seen in a liquid electrolyte using a solvent can be improved. However, a liquid is still used as the electrolyte, so there are the problems that handling is not easy at the time of production of an electrochemical device and, further, the problem of liquid leakage at the time of use is not completely solved.

Therefore, use of a polymer material which is excellent in ion conductivity as an electrolyte (a so-called "polymer electrolyte") has been studied. For example, Patent Document 2 proposes use, as an electrolyte composition, of a polyether compound which is comprised of a polyalkylene oxide main chain, ionic side chains, and counter ions of ionic side chains wherein the ionic side chains or counter ions exhibit liquid crystallinity. Further, Patent Document 3 proposes a solid electrolyte composition using a polymer compound which has cationic structures at the main chain or side chains and which has halide ions or polyhalide ions as counter anions of the cationic structures. These electrolyte compositions are solid in form exhibiting almost no fluidity in the normal usage environment of the electrolyte, so the problem of liquid leakage at the time of use of the electrochemical device is solved. Further, use formed into desired shapes by various shaping methods is possible, so compared with use of a liquid as an electrolyte, there is the advantage that handling at the time of production of an electrochemical device is easy.

However, there is the problem that the electrolyte composition which is described in Patent Document 2 and Patent Document 3 is not sufficient in ion conductivity. Further, it is a solid which exhibits almost no fluidity in the usual usage environment of an electrolyte, so preshaping is required to obtain the desired shape. There is also the problem that adjustment of the shape is difficult at the time of application to the electrochemical device. For this reason, a polymer material which has suitable fluidity to an extent enabling adjustment of the shape and further improved in ion conductivity is fervently desired.

PRIOR ART DOCUMENTS

Patent Documents

Patent Document 1: Japanese Patent Publication No. 2001-256828A
Patent Document 2: Japanese Patent Publication No. 2002-246066A
Patent Document 3: WO2004/112184

SUMMARY OF THE INVENTION

Problem to be Solved by the Invention

The present invention has as its object the provision of a polymer material which has suitable fluidity and further is excellent in ion conductivity.

Means for Solving the Problems

The inventors engaged in intensive research to achieve the above object and as a result discovered that by introducing cationic groups of specific structures to the side chains of a polyether compound and making the counter anions of the same specific anions and, further, by limiting the number of repeating units which form the polyether compound to a specific range, it is possible to obtain a polyether compound which has suitable fluidity and further is extremely excellent in ion conductivity. The present invention was completed based on this discovery.

Accordingly, according to the present invention, there is provided a polyether compound containing repeating units which are represented by the following general formula (1) in an average number per molecule of 10 to 100, which contains as at least part of the repeating units which are represented by the general formula (1), the repeating units which are represented by the following general formula (2).

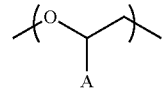

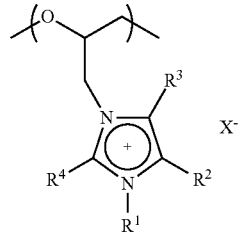

In the general formula (1), A is a monovalent group. In the general formula (2), $R^1$ to $R^4$ respectively independently are a hydrogen atom or a $C_1$ to $C_3$ alkyl group, and $R^2$ and $R^3$ may be bonded with each other. Further, in the general formula (2), $X^-$ is an anion which is comprised of 2 to 25 atoms.

In the above polyether compound, in the general formula (2), the anion which is represented by $X^-$ and is comprised of 2 to 25 atoms is preferably any of $OH^-$, $SCN^-$, $BF_4^-$, $PF_6^-$, $ClO_4^-$, $(FSO_2)_2N^-$, $(CF_3SO_2)_2N^-$, $(CF_3CF_2SO_2)_2N^-$, $CH_3SO_3^-$, $CF_3SO_3^-$, $CF_3COO^-$, and $PhCOO^-$.

In the above polyether compound, in the repeating units which are expressed by the general formula (1), the ratio of the repeating units which are represented by the general formula (2) is preferably 2 mol % or more.

In the above polyether compound, in the repeating units which are represented by the general formula (1), the units other than the repeating units which are represented by the general formula (2) preferably include at least one unit selected from units where the monovalent group which is represented by A in the general formula (1) is a hydrogen atom, units where it is an alkyl group, and units where it is a haloalkyl group, and units which have the same structure as the repeating units which are represented by the general formula (2) except anions where $X^-$ is comprised of a single atom.

Further, according to the present invention, there is provided an electrolyte composition which includes the above polyether compound.

Furthermore, according to the present invention, there is provided a method of production of a polyether compound, which method of production of a polyether compound comprising a step of ring opening polymerizing a monomer composition which contains epichlorohydrin in the presence of an onium salt of a compound which contains atoms of Group XV or Group XVI of the Periodic Table and trialkyl aluminum where all of the contained alkyl groups are linear alkyl groups so as to obtain an epichlorohydrin unit-containing polyether compound, a step of reacting the obtained epichlorohydrin unit-containing polyether compound with an imidazole compound so as to obtain an imidazolium chloride structure unit-containing polyether compound, and a step of reacting the obtained imidazolium chloride structure unit-containing polyether compound with a salt of an anion comprised of 2 to 25 atoms and a metal cation to perform an anion exchange reaction.

Effects of the Invention

According to the present invention, it is possible to obtain a polymer material which has suitable fluidity and is excellent in ion conductivity. Further, by using this polymer material as an electrolyte composition, it is possible to obtain an electrolyte which is easy to handle and is excellent in ion conductivity.

DESCRIPTION OF EMBODIMENTS

The polyether compound of the present invention contains repeating units which are represented by the following general formula (1) in an average number per molecule of 10 to 100, which contain as at least part of the repeating units which are represented by the general formula (1), repeating units which are represented by the following general formula (2).

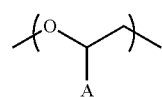
(1)

In the general formula (1), A is a monovalent group.

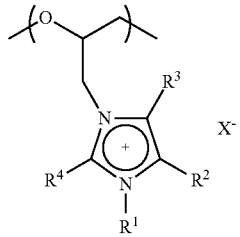
(2)

In the general formula (2), $R^1$ to $R^4$ respectively independently indicate a hydrogen atom or $C_1$ to $C_3$ alkyl group, and $R^2$ and $R^3$ may be bonded with each other. Further, in the general formula (2), $X^-$ is an anion which is comprised of 2 to 25 atoms.

The polyether compound of the present invention contains the repeating units which are represented by the general formula (1) (oxirane units) in an average number per molecule of 10 to 100, preferably 10 to 50. If this number is too small, the polyether compound becomes too high in fluidity and liquid leakage is liable to occur when it is used as an electrolyte. If this number is too large, the polyether compound loses fluidity and is liable to become inferior in ion conductivity.

Further, the polyether compound of the present invention contains, at least as part of the repeating units which are represented by the general formula (1), oxirane units which contain imidazolium structures represented by the general formula (2). To make the polyether compound of the present invention a polymer material which has suitable fluidity and which is excellent in ion conductivity, inclusion of the repeating units which are represented by the general formula (2) is necessary.

In the general formula (2), $R^1$ to $R^4$ respectively independently represent a hydrogen atom or $C_1$ to $C_3$ alkyl group. However, $R^2$ and $R^3$ may bond with each other to form a $C_2$ to $C_6$ alkylene group. As the $C_1$ to $C_3$ alkyl group, a methyl group, ethyl group, propyl group, or isopropyl group may be mentioned, while as the $C_2$ to $C_6$ alkylene group obtained by the $R^2$ and $R^3$ bonding with each other, a 1,2-ethylene group, 1,3-propylene group, 1,4-butylene group, 1,5-pentylene group, 1,6-hexylene group, 4-methyl-2,2-pentylene group, 2,3-dimethyl-2,3-butylene group, etc. may be illustrated. The groups represented by $R^1$ to $R^4$ may all be the same groups in the same repeating units or may be partially or completely different groups. Further, the polyether compound may contain different types of repeating units which are represented by the general formula (2) with different $R^1$ to $R^4$.

In the general formula (2), $X^-$ represents an anion which is comprised of 2 to 25 atoms and means a counter anion of an imidazolium structure. The number of atoms which forms this anion should be 2 to 25, but 2 to 20 is preferable and 2 to 15 is more preferable. If the anion which is represented by $X^-$ is comprised of a halide ion or other single atom or is comprised of an anionic mesogenic group or other group which is comprised of over 25 atoms, the obtained polyether compound is liable to be inferior in ion conductivity.

In the general formula (2), the type of the anion which is represented by $X^-$ is not particularly limited so long as it is comprised of 2 to 25 atoms, but as types which can particularly suitably be used, $OH^-$, $SCN^-$, $BF_4^-$, $PF_6^-$, $ClO_4^-$, $(FSO_2)_2N^-$, $(CF_3SO_2)_2N^-$, $(CF_3CF_2SO_2)_2N^-$, $CH_3SO_3^-$, $CF_3SO_3^-$, $CF_3COO^-$, and $PhCOO^-$ may be mentioned. Note that in the repeating units which are represented by the general formula (2) in the polyether compound as a whole, all of the anions which are represented by X⁻ may be the same types of anions or may comprise different types of anions mixed together.

The polyether compound of the present invention may be one where all of the repeating units which are represented by the general formula (1) are comprised of the repeating units which are represented by the general formula (2), but may also contain repeating units which are represented by the general formula (1) other than the repeating units which are represented by the general formula (2). As examples of repeating units which are represented by the general formula (1) other than the repeating units which are represented by the general formula (2), ethylene oxide units (case of general formula (1) wherein monovalent group represented by A is hydrogen atom); propylene oxide units, 1,2-butylene oxide units, and other units where the monovalent group represented by A in the general formula (1) is an alkyl group; epichlorohydrin units, epibromohydrin units, epiodohydrin units, and other units where the monovalent group represented by A in the general formula (1) is a haloalkyl group; methoxyethoxyethylglycidyl ether units and other units where the monovalent group represented by A in the general formula (1) is an ether group-containing group; allylglycidyl ether units and other units where the monovalent group represented by A in the general formula (1) is an alkenyl group-containing group; glycidyl acrylate units and other units where the monovalent group represented by A in the general formula (1) is an acrylic group-containing group; units which have the same structure as the repeating units which are represented by the general formula (2) other than ones where the counter anion (X⁻) is comprised of a single atom, etc. may be mentioned, but the invention is not limited to these. When the polyether compound of the present invention includes repeating units which are represented by the general formula (1) other than the repeating units which are represented by the general formula (2), among these as well, inclusion of repeating units which are represented by the general formula (1) which are selected from units where the monovalent group represented by A in the general formula (1) is a hydrogen atom, units where it is an alkyl group, units where it is a haloalkyl group, and units which have the same structures as the repeating units which are represented by the general formula (2) other than those where the counter anion (X⁻) is comprised of a single atom is preferable. Furthermore, among these as well, inclusion of repeating units which are represented by the general formula (1) which are selected from units where the monovalent group represented by A in the general formula (1) is a hydrogen atom (that is, ethylene oxide units), units where it is a methyl group (that is, propylene oxide units), units where it is a chloromethyl group (that is, epichlorohydrin units), and units which have the same structures as the repeating units which are represented by the general formula (2) other than those where the counter anion (X⁻) is comprised of a single atom is more preferable.

In the polyether compound of the present invention, among the repeating units which are represented by the general formula (1), the ratio which is occupied by the repeating units which are represented by the general formula (2) is not particularly limited. Usually, it is 2 mol % or more. 5 mol % or more is preferable, 10 mol % or more is more preferable, 20 mol % or more is further preferable, and 50 mol % is particularly preferable. If this ratio is too small, the obtained polyether compound is liable to be inferior in ion conductivity. Note that, in the polyether compound, when there are repeating units which are represented by the general formula (1) other than the repeating units which are represented by the general formula (2) (that is, when the above ratio is less than 100 mol %), the form of distribution of these plurality of repeating units is not particularly limited. A compound having a random distribution is preferable.

The polyether compound of the present invention may contain repeating units other than the repeating units which are represented by the general formula (1) as well. As examples of such repeating units, 2,3-butylene oxide units and other oxirane monomer units with two or more substituents and cyclohexene oxide and other oxirane monomer units which contain ring structures may be mentioned, but the invention is not limited to these. The ratio, with respect to all repeating units of the polyether compound of the present invention, of repeating units other than the repeating units which are represented by the general formula (1) is not particularly limited, but 10 mol % or less is preferable, 5 mol % or less is more preferable, and substantially 0 mol % is particularly preferable.

The end groups of the polyether compound of the present invention are not particularly limited and can be made any monovalent groups. As specific examples of groups forming the end groups, a hydrogen atom, halogen group, alkyl group, haloalkyl group, hydroxyl group, group represented by the following general formula (3), etc. may be mentioned. Among these as well, the compound in which one end group of the polyether compound is a hydroxyl group, while the other end group is a group represented by the general formula (3) is preferable.

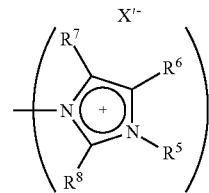

(3)

In the general formula (3), R⁵ to R⁸ respectively independently indicate a hydrogen atom or C₁ to C₃ alkyl group, and R⁶ and R⁷ may be bonded with each other. Further, in the general formula (3), X'⁻ is an anion comprised of 1 to 25 atoms.

The number average molecular weight of the polyether compound of the present invention is not particularly limited so long as the number of the repeating units is the one mentioned above, but 1000 to 50,000 is preferable, while 1000 to 40,000 is more preferable. Further, the molecular weight distribution, which is found as the ratio of the weight average molecular weight of the polyether compound to the number average molecular weight, is not particularly limited, but 1.0 to 4.0 is preferable, while 1.0 to 2.0 is more preferable.

The method of synthesis of the polyether compound of the present invention is not particularly limited. Any synthesis method may be employed so long as obtaining the target polyether compound. However, from the viewpoint of obtaining the target polyether compound more easily, the method of reacting a polyether compound which contains epichlorohydrin units with an imidazole compound so as to obtain an imidazolium chloride structure unit-containing polyether compound, then converting a chloride ion in the imidazolium chloride structure in accordance with an ordinary method of anion exchange to an anion which is comprised of 2 to 25 atoms.

The polyether compound which contains epichlorohydrin units can be synthesized by the known method of polymerization of epichlorohydrin so long as the target polymerization degree is obtained. Further, to react the polyether compound which contains polyepichlorohydrin units with an imidazole compound to replace at least part of the polyepichlorohydrin units with imidazolium chloride structure units, the known onium forming reaction can be applied. The known onium forming reaction is disclosed in Japanese Patent Publication No. 50-33271A, Japanese Patent Publication No. 51-69434A, Japanese Patent Publication No. 52-42481A, etc.

The method of converting a chloride ion in the imidazolium chloride structure of the imidazolium chloride structure unit-containing polyether compound to an anion which is comprised of 2 to 25 atoms is not particularly limited. The method of mixing an imidazolium chloride structure unit-containing polyether compound with a salt of the target anion which is comprised of 2 to 25 atoms and a metal cation for a reaction is preferable.

To obtain the polyether compound of the present invention, as a particular suitable method, the following method of production of the polyether compound of the present invention may be mentioned. That is, the method of production of the polyether compound of the present invention is a method of production of a polyether compound of the above-mentioned present invention which comprises (1) a step of ring opening polymerizing a monomer composition which contains epichlorohydrin in the presence of an onium salt of a compound which contains an atom of Group XV or Group XVI of the Periodic Table and trialkyl aluminum where all of the contained alkyl groups are linear alkyl groups so as to obtain an epichlorohydrin unit-containing polyether compound, (2) a step of reacting the obtained epichlorohydrin unit-containing polyether compound with an imidazole compound to obtain an imidazolium chloride structure unit-containing polyether compound, and (3) a step of reacting the obtained imidazolium chloride structure unit-containing polyether compound with a salt of an anion comprised of 2 to 25 atoms and a metal cation to perform an anion exchange reaction.

The first step in the method of production of the polyether compound of the present invention is the step of ring opening polymerizing a monomer composition which contains epichlorohydrin in the presence of a catalyst which is described in Japanese Patent Publication No. 2010-53217A, that is, a catalyst which contains an onium salt of a compound which contains an atom of Group XV or Group XVI of the Periodic Table and trialkyl aluminum where all of the contained alkyl groups are linear alkyl groups to obtain an epichlorohydrin unit-containing polyether compound. The monomer composition which is used may contain epichlorohydrin as at least part. If necessary, it may contain ethylene oxide, propylene oxide, 1,2-butylene oxide, allylglycidyl ether, and other monomers which can be copolymerized with epichlorohydrin.

As the onium salt of a compound which contains an atom of Group XV or Group XVI of the Periodic Table which is used as one of the ingredients of the catalyst, an ammonium salt, pyridinium salt, imidazolium salt, phosphonium salt, arsonium salt, stibonium salt, oxonium salt, sulfonium salt, and selenonium salt may be illustrated. Among these, an ammonium salt, pyridinium salt, imidazolium salt, phosphonium salt, and sulfonium salt are preferably used, an ammonium salt, phosphonium salt, and sulfonium salt are particularly preferably used, and an ammonium salt is most preferably used. Further, among the anmonium salts, tetranormal butylammonium bromide or tetranormal butylammonium borohydride are particularly preferable.

The amount of use of the onium salt of a compound which contains an atom of Group XV or Group XVI of the Periodic Table may be determined in accordance with the molecular weight targeted by the polyether-based polymer to be obtained. It is not particularly limited, but a suitable amount in the method of production of the polyether compound of the present invention is 0.0005 to 10 mol % with respect to the total monomer which is used.

The trialkyl aluminum where all of the contained alkyl groups are linear alkyl groups, which is used as another ingredient of the catalyst, is a compound comprised of aluminum to which three alkyl groups are bonded, wherein the three alkyl groups which are bonded with the aluminum are all linear alkyl groups. For example, methyl aluminum, triethyl aluminum, and trinormal octyl aluminum may be mentioned. Among these, trimethyl aluminum and triethyl aluminum are particularly preferably used.

The ratio of use of the onium salt of a compound which contains an atom of Group XV or Group XVI of the Periodic Table and trialkyl aluminum where all of the contained alkyl groups are linear alkyl groups is not particularly limited. The molar ratio of the onium salt:trialkyl aluminum is preferably 1:1 to 1:100 in range, more preferably 1.0:1.1 to 1.0:50.0 in range, particularly preferably 1.0:1.2 to 1.0:10.0 in range.

The method of mixing the onium salt of a compound which contains an atom of Group XV or Group XVI of the Periodic Table and trialkyl aluminum where all of the contained alkyl groups are linear alkyl groups is not particularly limited. It is preferable to dissolve or suspend these in a solvent and then mix them. The solvent used is not particularly limited. An inert solvent may be suitably used. For example, benzene, toluene, or other aromatic hydrocarbon; n-pentane, n-hexane, and other linear saturated hydrocarbons; cyclopentane, cyclohexane, and other alicyclic hydrocarbons; tetrahydrofuran, anisole, diethylether, and other ethers; or mixed solvents of these; etc. may be used. The temperature and time when mixing the ingredients of the catalyst are not particularly limited, but mixing under conditions of −30 to 50° C. for 10 seconds to 30 minutes is preferable.

In the ring opening polymerization of a monomer composition containing epichlorohydrin in the presence of a catalyst comprised of the above two ingredients, the method of mixing the catalyst and the monomer is not particularly limited. For example, the monomer composition may be added to a solvent containing the catalyst or the catalyst may be added to a solvent containing the monomer composition. The polymerization method is not particularly limited. From the viewpoint of controlling the polymerization well, use of the solution polymerization method for polymerization is preferred. As the solvent, an inert solvent is preferably used. For example, benzene, toluene, or other aromatic hydrocarbon; n-heptane, n-hexane, or other linear saturated hydrocarbon; cyclopentane, cyclohexane, or other alicyclic hydrocarbon; tetrahydrofuran, anisole, diethylether, or other ether; or a mixed solvent of these; etc. may be used. Among these solvents, since the polymerization reaction rate is fast, a nonpolar solvent is particularly preferably used. The amount of use of the solvent is not particularly limited, but use giving a concentration of the monomer composition of 1 to 50 wt % is preferable, while use giving 3 to 40 wt % is particularly preferable.

The conditions for polymerization are not particularly limited and may be determined in accordance with the type of the monomer or catalyst used or targeted molecular weight. The pressure at the time of polymerization is usually 1 to 500 atm, preferably 1 to 100 atm, particularly preferably 1 to 50 atm. The temperature at the time of polymerization is usually −70 to 200° C., preferably −40 to 150° C., particularly preferably −20 to 100° C. The polymerization time is usually 10 seconds to 100 hours, preferably 20 seconds to 80 hours, particularly preferably 30 seconds to 50 hours.

In the method of production of the polyether compound of the present invention, as explained above, by using the catalyst which contains the onium salt of a compound which contains an atom of Group XV or Group XVI of the Periodic Table and trialkyl aluminum where all of the contained alkyl groups are linear alkyl groups, the polymerization reaction proceeds with a living property, so control of the polymerization becomes easy and, as a result, production of an epichlorohydrin unit-containing polyether compound with the desired polymerization degree becomes easy.

The second step in the method of production of the polyether compound of the present invention is a step of reacting the epichlorohydrin unit-containing polyether compound which was obtained in the above way with an imidazole compound (quaternary reaction) to convert the chloro groups of the epichlorohydrin units to imidazolium chloride structure-containing groups to obtain an imidazolium chloride structure unit-containing polyether compound.

The imidazole compound which is used is an imidazole compound which corresponds to the imidazolium structures contained in the repeating units which are represented by the general formula (2). As specific examples, imidazole, 1-methylimidazole, 1,2-dimethylimidazole, etc. may be mentioned.

The method of mixing the epichlorohydrin unit-containing polyether compound and the imidazole compound is not particularly limited. For example, the method of adding and mixing an imidazole compound in a solution which contains a polyether compound, the method of adding and mixing a polyether compound in a solution which contains an imidazole compound, the method of preparing an imidazole compound and polyether compound as separate solutions and mixing the two solutions, etc. may be mentioned.

As the solvent, an inert solvent is preferably used. A nonpolar one or a polar one are both possible. As a nonpolar solvent, for example, benzene, toluene, and other aromatic hydrocarbons; n-pentane, n-hexane, and other linear saturated hydrocarbons; cyclopentane, cyclohexane, and other alicyclic saturated hydrocarbons; etc. may be mentioned. As polar solvents, tetrahydrofuran, anisole, diethylether, and other ethers; ethyl acetate, ethyl benzoate, and other esters; acetone, 2-butanone, acetophenone, and other ketones; acetonitrile, dimethylformamide, dimethylsulfoxide, and other aprotonic polar solvents; ethanol, methanol, water, and other protonic polar solvents; etc. may be mentioned. As solvents, these mixed solvents may also be suitably used. The amount of use of the solvent is not particularly limited, but use giving a concentration of the polyether compound of 1 to 50 wt % is preferable. Use giving 3 to 40 wt % is more preferable.

The amount of use of the imidazole compound is not particularly limited and may be determined in accordance with the ratio of the content of the imidazolium chloride structure units of the targeted polyether compound etc. Specifically, the amount of use of the imidazole compound is usually 0.01 to 100 moles with respect to 1 mole of the epichlorohydrin units of the epichlorohydrin unit-containing polyether compound, preferably 0.02 to 50 moles, more preferably 0.03 to 10 moles, furthermore preferably 0.05 to 2 moles in range.

The pressure when reacting the polyether compound and the imidazole compound is not particularly limited. It is usually 1 to 500 atm, preferably 1 to 100 atm, particularly preferably 1 to 50 atm. The temperature at the time of reaction is also not particularly limited and is usually 0 to 200° C., preferably 20 to 170° C., more preferably 40 to 150° C. The reaction time is usually 1 minute to 1,000 hours, preferably 3 minutes to 800 hours, more preferably 5 minutes to 500 hours, furthermore preferably 30 minutes to 200 hours.

The third step in the method of production of the polyether compound of the present invention is the step of reacting the imidazolium chloride structure unit-containing polyether compound which was obtained in the above way with a salt of an anion which is comprised of 2 to 25 atoms and a metal cation to perform an anion exchange reaction and convert the counter anions, that is, chloride ions, of the imidazolium structure of the polyether compound to anions which are comprised of 2 to 25 atoms.

The salt of an anion which is comprised of 2 to 25 atoms and a metal cation is a salt of the counter anion (X⁻) which is contained in the repeating units which are represented by the general formula (2) of the targeted polyether compound of the present invention and a metal cation and may be selected in accordance with the desired counter anions (X⁻). As specific examples of the salt which is used, potassium hydroxide (KOH), lithium(bistrifluoromethylsulfone)imide ($Li(CF_3SO_2)_2N$), lithium (bisfluorosulfone)imide ($Li(FSO_2)_2N$), lithiumtetrafluoroborate ($LiBF_4$), lithiumthiocyanate (LiSCN), lithiumhexafluorophosphate ($LiPF_6$), lithiumperchlorate ($LiClO_4$), lithium(bispentafluoroethylsulfone)imide ($Li(CF_3CF_2SO_2)_2N$), lithiummethylsulfonate ($LiCH_3SO_3$), lithiumtrifluoromethylsulfonate ($LiCF_3SO_3$), lithiumtrifluoroacetate ($CF_3COOLi$), lithiumbenzoate (Ph-COOLi), etc. may be mentioned.

The conditions for performing the anion exchange reaction are not particularly limited. It is possible to mix just the imidazolium chloride structure unit-containing polyether compound and the salt of an anion which is comprised of 2 to 25 atoms and a metal cation or possible to do this under conditions of the presence of an organic solvent or other compound. Further, the amount of use of the salt is not particularly limited, but is usually 0.01 to 100 moles with respect to 1 mole of the imidazolium chloride structure units of the imidazolium chloride structure unit-containing polyether compound used, preferably 0.02 to 50 moles, more preferably 0.03 to 10 moles in range.

The pressure at the time of the anion exchange reaction is usually 1 to 500 atm, preferably 1 to 100 atm, particularly preferably 1 to 50 atm. The temperature at the time of the reaction is usually −30 to 200° C., preferably −15 to 180° C., more preferably 0 to 150° C. The reaction time is usually 1 minute to 1000 hours, preferably 3 minutes to 100 hours, more preferably 5 minutes to 10 hours, furthermore preferably 5 minutes to 3 hours.

After the anion exchange reaction is completed, for example drying in vacuo or other ordinary method may be followed to recover the targeted polyether compound.

For example, the polyether compound of the present invention which is obtained in the above way has excellent ion conductivity and suitable fluidity. Therefore, the polyether compound of the present invention is suitable as a material of an electrolyte composition which is used for, for example, a secondary cell, fuel cell, dye-sensitized solar cell, actuator, or other electrochemical device etc. That is, the electrolyte composition of the present invention is one which contains the polyether compound of the present invention.

The electrolyte composition of the present invention may be one which is comprised of only the polyether compound of the present invention or more may be one to which other materials or additives are added. As the ingredients other than the polyether compound of the present invention which can be added to the electrolyte composition of the present invention, $LiPF_6$, LiTFSI, KI, and other metal salts, water, methanol, ethylene carbonate, and other low molecular weight compounds, ionic liquids, carbon materials and inorganic materials and other fillers may be mentioned, but the invention is not limited to these.

EXAMPLES

Below, examples and comparative examples will be given to more specifically explain the present invention. Note that, the "parts" and "%" in the examples are based on weight unless otherwise indicated.

The various measurements were performed based on the following methods.

[Number Average Molecular Weight (Mn) and Molecular Weight Distribution (Mw/Mn)]

Gel permeation chromatography (GPC) using dimethylformamide as a solvent was used for measurement as a value converted to polystyrene. Note that, as the measuring device, HLC-8320 (made by Toso) was used. As the column, two TSKgelα-M (made by Toso) were used connected in series. For the detector, a differential refractometer RI-8320 (made by Toso) was used.

[Volume Specific Resistance Value]

For the sample coin shaped cell, as a measuring system, an Impedance Analyzer Model 1260 and Potentiostat Model 1287 (both made by Solartron) were combined for use to measure the volume specific resistance value. Note that the measurement voltage amplitude was 100 mV, the measurement frequency range was 1 MHz to 0.1 Hz, and the measurement was conducted under a dry atmosphere of 25° C. and humidity 0% using an SUS304 electrode as the main electrode. The lower the volume specific resistance value, the better the ion conductivity.

Production Example A

Living Anion Polymerization of Epichlorohydrin

To a glass reactor equipped with a stirrer and with an inside substituted by argon, tetranormal butylammonium bromide 3.22 g and toluene 50 ml were added. This was cooled to 0° C. Next, triethyl aluminum 1.256 g (1.1 equivalents with respect to tetranormal butylammonium bromide) dissolved in normal hexane 10 ml was added. This was reacted for 15 minutes to obtain a catalyst composition. To the obtained catalyst composition, epichlorohydrin 10.0 g was added. The polymerization reaction was performed at 0° C. After the start of the polymerization reaction, the viscosity of the solution gradually rose. After 12 hours reaction, a small amount of water was poured into the polymerization reaction solution to stop the reaction. The obtained polymerization reaction solution was washed by 0.1N hydrochloric acid aqueous solution to remove the catalyst residue. Furthermore, this was washed by ion exchanged water, then the organic phase was dried in vacuo at 50° C. for 12 hours. The yield of the colorless, transparent oily substance obtained due to this was 9.9 g. Further, the number average molecular weight (Mn) by GPC of the obtained substance was 1,050, while the molecular weight distribution (Mw/Mn) was 1.35. From the above, the oily substance which was obtained can be said to be an oligomer which had a bromomethyl group at the polymerization initiation end and had a hydroxyl group at the polymerization termination end and is comprised of epichlorohydrin units (average 11-mer).

Production Example B

Quaternization of Epichlorohydrin Oligomer by 1-Methylimidazole

The epichlorohydrin oligomer which was obtained in Production Example A, 5.0 g, 1-methylimidazole 12.1 g, and acetonitrile 10.0 g were added to a glass reactor equipped with a stirrer substituted with argon and heated to 80° C. After reaction at 80° C. for 48 hours, the solution was cooled to room temperature to stop the reaction. The obtained reaction product was washed by an equal weight mixed solvent of toluene/methanol/water, then the organic phase including 1-methylimidazole and toluene was removed and the aqueous phase was dried in vacuo at 50° C. for 12 hours, whereupon a light reddish solid 9.4 g was obtained. This solid was measured by $^1$H-NMR and elementary analysis, whereupon it was identified as an imidazolium structure-containing polyether compound which has halide ions as counter anions wherein all of the chloro groups of the repeating units of the starting material epichlorohydrin oligomer were substituted by 1-methylimidazolium groups which have chloride ions as counter anions and the bromo group of the bromomethyl group of the polymerization initiation end was exchanged with a 1-methylimidazolium group which has a bromide ion as a counter anion.

Production Example 1

Anion Exchange of Imidazolium Structure-Containing Polyether Compound which has Halide Ions as Counter Anions by Potassium Hydroxide The imidazolium structure-containing polyether compound which has halide ions as counter anions which was obtained at Production Example B, 2.5 g, potassium hydroxide 2.0 g, and ion exchanged water 20 ml were added to a glass reactor equipped with a stirrer. These were allowed to react at room temperature for 30 minutes, then the solution was dried in vacuo at 50° C. for 1 hour, whereupon a light reddish oily substance was obtained. The obtained oily substance was dissolved in a methanol/acetone/THF mixed solvent, the remaining undissolved crystalline insolubles were separated, then the result was dried in vacuo at 50° C. for 1 hour, whereupon a light reddish high viscosity oily substance was obtained. The obtained solid was again dissolved in a methanol/acetone/THF mixed solvent, the remaining undissolved crystalline insolubles were separated, then the result were dried in vacuo at 50° C. for 12 hours, whereupon a light reddish high viscosity oily substance 2.0 g was obtained. The obtained oily substance was measured by Fourier transform infrared spectrometry and elemental analysis, whereupon it was identified as an imidazolium structure-containing polyether compound which has hydroxide ions as counter anions wherein all of the chloride ions and 50 mol % of the bromide ions of the starting material imidazolium structure-containing polyether compound which has halide ions as counter anions were exchanged with hydroxide ions.

Production Example 2

Anion Exchange of Imidazolium Structure-Containing Polyether Compound which has Halide Ions as Counter Anions by Lithium(Bistrifluoromethylsulfone)Imide The imidazolium structure-containing polyether compound which has halide ions as counter anions which was obtained at Production Example B, 2.5 g, lithium(bistrifluoromethylsulfone)imide 4.1 g, and ion exchanged water 20 ml were added to a glass reactor equipped with a stirrer. These were allowed to react at room temperature for 30 minutes, then the solution was dried in vacuo at 50° C. for 12 hours. The obtained solid-liquid mixture was washed with water to remove the inorganic salts, then the liquid phase was extracted by toluene. The obtained toluene solution was dried in vacuo at 50° C. for 12 hours, whereupon a substantially colorless, transparent, viscous liquid substance 5.7 g was obtained. The obtained viscous liquid substance was measured by $^1$H-NMR spectrometry and elemental analysis, whereupon it was identified as an imidazolium structure-containing polyether compound which has (bistrifluoromethylsulfone)imide anions as counter ions wherein all of the chloride ions and bromide ions of the starting material imidazolium structure-containing polyether compound which has halide ions as counter anions are exchanged with (bistrifluoromethylsulfone)imide anions.

Production Example 3

Anion Exchange of Imidazolium Structure-Containing Polyether Compound which has Halide Ions as Counter Anions by Lithium (Bisfluorosulfone)Imide The imidazolium structure-containing polyether compound which has halide ions as counter anions which was obtained at Production Example B, 2.5 g, lithium(bisfluorosulfone)imide 2.9 g, and ion exchanged water 20 mil were added to a glass reactor equipped with a stirrer. They were allowed to react at room temperature for 30 minutes, then the solution was dried in vacuo at 50° C. for 12 hours. The obtained solid-liquid mixture was washed by water to remove the inorganic salt, then the liquid phase was extracted by toluene. The obtained toluene solution was dried in vacuo at 50° C. for 12 hours, whereupon a substantially colorless, transparent viscous liquid substance 4.3 g was obtained. The obtained viscous liquid substance was measured by $^1$H-NMR spectrometry and elemental analysis, whereupon it was identified as an imidazolium structure-containing polyether compound which has (bisfluorosulfone)imide anions as counter ions wherein all of the chloride ions and bromide ions of the starting material imidazolium structure-containing polyether compound which has halide ions as counter anions are exchanged with (bisfluorosulfone)imide anions.

Production Example 4

Anion Exchange of Imidazolium Structure-Containing Polyether Compound which has Halide Ions as Counter Anions by Lithium Tetrafluoroborate The imidazolium structure-containing polyether compound which has halide ions as counter anions which was obtained in Production Example B, 2.5 g, lithiumtetrafluoroborate 2.9 g, and tetrahydrofuran 20 ml were added to a glass reactor equipped with a stirrer. This was allowed to react at room temperature for 30 minutes, then was dried in vacuo at 50° C. for 12 hours. The liquid phase was extracted by toluene. The obtained toluene solution was dried in vacuo at 50° C. for 12 hours, whereupon a substantially colorless, transparent viscous liquid substance 4.3 g was obtained. The obtained viscous liquid substance was measured by $^1$H-NMR spectrometry, whereupon it was identified as an imidazolium structure-containing polyether compound which has tetrafluoroborate anions as counter anions wherein all of the chloride ions and bromide ions of the starting material imidazolium structure-containing polyether compound which has halide ions as counter anions were exchanged with tetrafluoroborate anions.

Production Example C

Partial Quaternization of Epichlorohydrin Oligomer by 1-Methylimidazole

The epichlorohydrin oligomer which was obtained in Production Example A, 5.0 g, 1-methylimidazole 2.7 g, and acetonitrile 10.0 g were added to a glass reactor equipped with a stirrer and with an inside substituted by argon and heated to 80° C. They were allowed to react at 80° C. for 96 hours, then the solution was cooled to room temperature and the reaction stopped. The obtained reaction product was washed by an equal weight mixed solution of toluene/methanol/water, then the organic phase containing the 1-methylimidazole and toluene was removed and the aqueous phase was dried in vacuo at 50° C. for 12 hours, whereupon a light reddish solid 9.4 g was obtained. This solid was measured by $^1$H-NMR, whereupon it was identified as an imidazolium structure-containing polyether compound which has halide ions as counter anions wherein 64 mol % of the chloro groups of the repeating units of the starting material epichlorohydrin oligomer were substituted by 1-methylimidazolium groups which have chloride ions as counter anions and 64 mol % of the bromo groups of the bromomethyl groups of the polymerization initiation ends were substituted by 1-methylimidazolium groups which have bromide ions as counter anions.

Production Example 5

Anion Exchange of Imidazolium Structure-Containing Polyether Compound which has Halide Ions as Counter Anions by Lithium(Bistrifluoromethylsulfone)Imide The imidazolium structure-containing polyether compound which has halide ions as counter anions which was obtained at Production Example C, 2.5 g, lithium(bistrifluoromethylsulfone)imide 1.5 g, and ion exchanged water 20 ml were added to a glass reactor equipped with a stirrer. These were allowed to react at room temperature for 30 minutes, then the solution was dried in vacuo at 50° C. for 12 hours. The obtained solid-liquid mixture was washed with water to remove the inorganic salts, then the liquid phase was extracted by toluene. The obtained toluene solution was dried in vacuo at 50° C. for 12 hours, whereupon a substantially colorless, transparent viscous liquid substance 4.9 g was obtained. The obtained viscous liquid substance was measured by $^1$H-NMR spectrometry, whereupon it was identified as an imidazolium structure-containing polyether compound which has (bistrifluoromethylsulfone)imide anions as counter anions wherein all of the counter anions of chloride ions and bromide ions of the starting material imidazolium structure-containing polyether compound which has halide ions as counter anions were exchanged with (bistrifluoromethylsulfone)imide anions.

Production Example D

Living Anion Polymerization of Epichlorohydrin and Quaternization of Obtained Epichlorohydrin Oligomer by 1-Methylimidazole Except for changing the amount of use of triethyl aluminum to 1.370 g (1.1 equivalents with respect to tetranormal butylammonium bromide), the amount of use of toluene to 50 ml, and the amount of use of epichlorohydrin to 50.0 g, the same procedure was followed as in Production Example A to perform a polymerization operation. The yield of the colorless, transparent oily substance which was obtained in this way was 48.5 g. Further, the number average molecular weight (Mn) of the obtained substance by GPC was 5,250, while the molecular weight distribution (Mw/Mn) was 1.18.

From the above, the oily substance which was obtained by the above can be said to be an oligomer which has a bromomethyl group at the polymerization initiation end, has a hydroxyl group at the polymerization termination end, and is comprised of epichlorohydrin units (average 57-mer). Next, the obtained epichlorohydrin oligomer 4.5 g was made to react in the same way as the Production Example B, whereupon a light reddish solid 9.4 g was obtained. This solid was measured by $^1$H-NMR and elemental analysis, whereupon it was identified as an imidazolium structure-containing polyether compound which has halide ions as counter anions wherein all of the chloro groups in the repeating units of the starting material epichlorohydrin oligomer were exchanged with 1-methylimidazolium groups which have chloride ions as counter anions and the bromo group of the bromomethyl group of the polymerization initiation end was exchanged with an 1-methylimidazolium group which has a bromide ion as a counter anion.

Production Example 6

Anion Exchange of Imidazolium Structure-Containing Polyether Compound which has Halide Ions as Counter Anions by Lithium(Bistrifluoromethylsulfone)Imide Except for using as the imidazolium structure-containing polyether compound which has halide ions as counter anions, instead of the one which was obtained in Production Example B, the one which was obtained in Production Example D in 2.5 g, the same procedure was followed as in Production Example 2, whereupon a substantially colorless, transparent, viscous liquid substance 5.7 g was obtained. The obtained viscous liquid substance was measured by $^1$H-NMR spectrometry and elemental analysis, whereupon it was identified as an imidazolium structure-containing polyether compound which has (bistrifluoromethylsulfone) imide anions as counter anions wherein all of the chloride ions and bromide ions of the starting material imidazolium structure-containing polyether compound which has halide ions as counter anions were exchanged with (bistrifluoromethylsulfone)imide anions.

Production Example E

Living Anion Polymerization of Epichlorohydrin and Propylene Oxide and Quaternization of Obtained Copolymerized Oligomer by 1-Methylimidazole Except for using, instead of epichlorohydrin 10.0 g, a mixture of epichlorohydrin 8.0 g and propylene oxide 2.0 g, the same procedure was followed as in Production Example A to perform a polymerization operation. The yield of the colorless, transparent oily substance which was obtained by this was 9.9 g. Further, the number average molecular weight (Mn) of the obtained substance by GPC was 1,200, while the molecular weight distribution (Mw/Mn) was 1.24. The oily substance which was obtained by the above can be said to be an oligomer which has a bromomethyl group at the polymerization initiation end, has a hydroxyl group at the polymerization termination end, and is comprised of a random copolymerized structure of epichlorohydrin units and propylene oxide units (14-mer comprised of average ten epichlorohydrin units and four propylene oxide units). Next, the obtained copolymerized oligomer 5.0 g was made to react in the same way as Production Example B, whereupon a light reddish powdery solid 8.5 g was obtained. This solid was measured by $^1$H-NMR and elemental analysis, whereupon it was identified as an imidazolium structure-containing copolymerized polyether compound which has halide ions as counter anions wherein all of the chloro groups in the epichlorohydrin units of the starting material copolymerized oligomer were exchanged with 1-methylimidazolium groups which have chloride ions as counter anions and the bromo group of the bromomethyl group of the polymerization initiation end was exchanged with a 1-methylimidazolium group which has a bromide ion as a counter anion.

Production Example 7

Anion Exchange of Imidazolium Structure-Containing Copolymerized Polyether Compound which has Halide Ions as Counter Anions by Lithium(Bistrifluoromethylsulfone)Imide Except for using as the imidazolium structure-containing polyether compound which has halide ions as counter anions, instead of the one which was obtained in Production Example B, the one which was obtained in Production Example E in 2.5 g, the same procedure was followed as in Production Example 2, whereupon a substantially colorless, transparent, viscous liquid substance 5.4 g was obtained. The obtained viscous liquid substance was measured by $^1$H-NMR spectrometry and elemental analysis, whereupon it was identified as an imidazolium structure-containing polyether compound which has (bistrifluoromethylsulfone) imide anions as counter anions wherein all of the chloride ions and bromide ions of the starting material imidazolium structure-containing copolymerized polyether compound which has halide ions as counter anions were exchanged with (bistrifluoromethylsulfone)imide anions.

Production Example F

Living Anion Polymerization of Epichlorohydrin and Propylene Oxide and Quaternization of Obtained Copolymerized Oligomer by 1-Methylimidazole Except for using, instead of epichlorohydrin 10.0 g, a mixture of epichlorohydrin 6.0 g and propylene oxide 4.0 g, the same procedure was followed as in Production Example A to perform a polymerization operation. The yield of the colorless, transparent oily substance which was obtained by this was 9.8 g. Further, the number average molecular weight (Mn) of the obtained substance by GPC was 1,200, while the molecular weight distribution (Mw/Mn) was 1.20. From the above, the obtained oily substance can be said to be an oligomer which has a bromomethyl group at the polymerization initiation end, has a hydroxyl group at the polymerization termination end, and is comprised of random copolymerized structures of epichlorohydrin units and propylene oxide units (16-mer comprised of average eight epichlorohydrin units and eight propylene oxide units). Next, the obtained copolymerized oligomer 5.0 g was similarly reacted in the same way as the Production Example B, whereupon a light reddish powdery solid 6.7 g was obtained. This solid was measured by $^1$H-NMR and elemental analysis, whereupon it was identified as an imidazolium structure-containing copolymerized polyether compound which has halide ions as counter anions wherein all of the chloro groups in the epichlorohydrin units of the starting material copolymerized oligomer were exchanged with 1-methylimidazolium groups which have chloride ions as counter anions and the bromo group of the bromomethyl group of the polymerization initiation end was exchanged with a 1-methylimidazolium group which has a bromide ion as a counter anion.

Production Example 8

Anion Exchange of Imidazolium Structure-Containing Copolymerized Polyether Compound which has Halide Ions as Counter Anions by Potassium Hydroxide Except for using as the imidazolium structure-containing polyether compound which has halide ions as counter anions, instead of the one which is obtained in the Production Example B, the one which was obtained in the Production Example E in 2.5 g, the same procedure was performed as in Production Example 1 whereupon a light reddish viscous liquid substance 2.1 g was obtained. The obtained viscous liquid substance was measured by $^1$H-NMR spectrometry and elemental analysis, whereupon it was identified as an imidazolium structure-containing polyether compound which has hydroxide ions as counter anions wherein all of the chloride ions and bromide ions of the starting material imidazolium structure-containing copolymerized polyether compound which has halide ions as counter anions were exchanged with hydroxide ions.

Production Example G

Living Anion Polymerization of Epichlorohydrin and Propylene Oxide and Quaternization of Obtained Copolymerized Oligomer by 1-Methylimidazole Except for using, instead of epichlorohydrin 10.0 g, a mixture of epichlorohydrin 9.0 g and propylene oxide 1.0 g and changing the amount of use of tetranormal butylammonium bromide to 0.322 g, the amount of use of triethyl aluminum to 0.148 g (1.3 equivalents with respect to tetranormal butylammonium bromide), and the amount of use of normal hexane to 3 ml, the same procedure was followed as in Production Example A to perform a polymerization operation. The yield of the colorless, transparent oily substance which was obtained by this was 9.9 g. Further, the number average molecular weight (Mn) of the obtained substance by GPC was 10,500, while the molecular weight distribution (Mw/Mn) was 1.10. From the above, the obtained oily substance can be said to be an oligomer which has a bromomethyl group at the polymerization initiation end, has a hydroxyl group at the polymerization termination end, and is comprised of random copolymerized structures of epichlorohydrin units and propylene oxide units (98-mer comprised of average 83 epichlorohydrin units and 15 propylene oxide units). Next, the obtained copolymerized oligomer 5.0 g was similarly reacted in the same way as the Production Example B, whereupon a light reddish powdery solid 8.9 g was obtained. This solid was measured by $^1$H-NMR and elemental analysis, whereupon it was identified as an imidazolium structure-containing copolymerized polyether compound which has halide ions as counter ions wherein all of the chloro groups in the epichlorohydrin units of the starting material copolymerized oligomer were exchanged with 1-methylimidazolium groups which have chloride ions as counter anions and the bromo group of the bromomethyl group of the polymerization initiation end was exchanged with a 1-methylimidazolium group which has a bromide ion as a counter anion.

Production Example 9

Anion Exchange of Imidazolium Structure-Containing Copolymerized Polyether Compound which has Halide Ions as Counter Anions by Lithium(Bistrifluoromethylsulfone)Imide Except for using as the imidazolium structure-containing polyether compound which has halide ions as counter anions, instead of the one which is obtained in the Production Example B, the one which was obtained in the Production Example G in 2.5 g, the same procedure was performed as in Production Example 2 whereupon a colorless, transparent viscous liquid substance 5.5 g was obtained. The obtained viscous liquid substance was measured by $^1$H-NMR spectrometry and elemental analysis, whereupon it was identified as an imidazolium structure-containing polyether compound which has (bistrifluoromethylsulfone)imide anions as counter anions wherein all of the chloride ions and bromide ions of the starting material imidazolium structure-containing copolymerized polyether compound which has halide ions as counter anions were exchanged with (bistrifluoromethylsulfone)imide anions.

Comparative Production Example 3

Anion Exchange of Imidazolium Structure-Containing Polyether Compound which has Halide Ions as Counter Anions by Potassium Iodide The imidazolium structure-containing polyether compound which has halide ions as counter anions which was obtained at Production Example B, 2.5 g, potassium iodide 2.4 g, and ion exchanged water 20 ml were added to a glass reactor equipped with a stirrer. These were allowed to react at room temperature for 30 minutes, then the solution was dried in vacuo at 50° C. for 1 hour, whereupon a light reddish oily substance was obtained. The obtained oily substance was dissolved in a methanol/acetone/THF mixed solvent, the remaining undissolved crystalline insolubles were separated, then the result was dried in vacuo at 50° C.

for 1 hour, whereupon a light reddish fine powdery solid was obtained. The obtained solid was again dissolved in a methanol/acetone/THF mixed solvent, the remaining undissolved crystalline insolubles were separated, then the result was dried in vacuo at 50° C. for 12 hours, whereupon a light reddish fine powdery solid 3.5 g was obtained. The obtained powdery solid was measured by elemental analysis, whereupon it was identified as an imidazolium structure-containing polyether compound which has iodide ions as counter anions wherein all of the chloride ions and 50 mol % of the bromide ions of the starting material imidazolium structure-containing polyether compound which has halide ions as counter anions were exchanged with iodide ions.

Comparative Production Example 4

Anion Exchange of Imidazolium Structure-Containing Copolymerized Polyether Compound which has Halide Ions as Counter Anions by Sodium 10-[Oxyphenyl-4-(p-Carbonitrilephenyl)]-1-Decane Sulfonate The imidazolium structure-containing copolymerized polyether compound which has halide ions as counter anions which was obtained at Production Example F, 2.5 g, sodium 10-[oxyphenyl-4-(p-carbonitrilephenyl)]-1-decanesulfonate 5.0 g, and ion exchanged water 20 ml were added to a glass reactor equipped with a stirrer. These were allowed to react at room temperature for 30 minutes, then the solution was dried in vacuo at 50° C. for 1 hour, whereupon a light reddish solid was obtained. The obtained solid was dissolved in a methanol/acetone/THF mixed solvent, the remaining undissolved crystalline insolubles were separated, then the result was dried in vacuo at 50° C. for 1 hour, whereupon a light reddish soft solid was obtained. The obtained solid was again dissolved in a methanol/acetone/THF mixed solvent, the remaining undissolved crystalline insolubles were separated, then the result was dried in vacuo at 50° C. for 12 hours, whereupon a light reddish soft solid 4.6 g was obtained. The obtained solid was measured by $^1$H-NMR spectrometry, whereupon it was identified as an imidazolium structure-containing polyether compound which has 10-[oxyphenyl-4-(p-carbonitrilephenyl)]-1-decanesulfonic acid ions as counter anions wherein all of the chloride ions and 50 mol % of the bromide ions of the starting material imidazolium structure-containing copolymerized polyether compound which has halide ions as counter anions were exchanged with 10-[oxyphenyl-4-(p-carbonitrilephenyl)]-1-decanesulfonic acid ions.

Comparative Production Example H Living Anion Polymerization of Epichlorohydrin and Propylene Oxide and Quaternization of Obtained Polymer by 1-Methylimidazole Except for changing the amount of use of tetranormal butylammonium bromide to 0.064 g, changing the amount of use of triethyl aluminum to 0.030 g (1.3 equivalents with respect to tetranormal butylammonium bromide), and changing the amount of use of normal hexane to 1 ml, the same procedure was followed as in Production Example A to perform a polymerization operation. The yield of the colorless, transparent oily substance which was obtained by this was 19.5 g. Further, the number average molecular weight (Mn) of the obtained substance by GPC was 95,500, while the molecular weight distribution (Mw/Mn) was 1.30.

From the above, the oily substance which was obtained can be said to have bromomethyl groups at the polymerization initiation ends, have hydroxyl groups at the polymerization termination ends, and be a polymer which is comprised of epichlorohydrin units (average 1032-mer). Next, the obtained polymer 5.0 g was reacted in the same way as Production Example B except for changing the amount of use of 1-methylimidazole to 24.2 g and the reaction time to 240 hours, whereupon a light reddish powdery solid 8.9 g was obtained. This solid was measured by $^1$H-NMR and elemental analysis, whereupon it was identified as an imidazolium structure-containing high molecular weight polyether compound which has halide ions as counter anions wherein all of the chloro groups in the epichlorohydrin units of the starting material epichlorohydrin polymer were exchanged with 1-methylimidazolium groups which have chloride ions as counter anions and the bromo group of the bromomethyl group of the polymerization initiation end was exchanged with a 1-methylimidazolium group which has a bromide ion as a counter anion.

Comparative Production Example 5

Anion Exchange of Imidazolium Structure-Containing High Molecular Weight Polyether Compound which has Halide Ions as Counter Anions by Lithium(Bistrifluoromethylsulfone)Imide Except for using, instead of the imidazolium structure-containing polyether compound which has halide ions as counter anions which was obtained in Production Example B, an imidazolium structure-containing high molecular weight polyether compound which has halide ions as counter anions which was obtained in Comparative Production Example H, in 2.5 g, for the same procedure as in Production Example 2, whereupon a colorless, transparent rubbery solid 5.7 g was obtained. The obtained solid was measured by $^1$H-NMR spectrometry and elemental analysis, whereby it was identified as an imidazolium structure-containing high molecular weight polyether compound which has (bistrifluoromethylsulfone)imide anions as counter anions wherein all of the chloride ions and bromide ions of the starting material imidazolium structure-containing high molecular weight polyether compound which have halide ions as counter anions were exchanged with (bistrifluoromethylsulfone)imide anions.

Comparative Production Example I

Production of Imidazolium-Modified Polyether Rubber

The inside of a sealed pressure resistant glass vessel was substituted with nitrogen and charged with toluene 200 parts and triisobutyl aluminum 60 parts. This glass bottle was immersed in ice water for cooling, then diethylether 230 parts was added and the mixture stirred. Next, this was cooled by ice water while adding phosphoric acid 13.6 parts and the result was further stirred. At this time, due to the reaction between triisobutyl aluminum and phosphoric acid, the pressure inside the vessel rose, so the pressure was suitably reduced. The obtained reaction mixture was reacted for aging in a 60° C. warm water bath for 1 hour to obtain a catalyst solution. Next, an autoclave was charged with epichlorohydrin 223.5 parts, ethylene oxide 30.3 parts, and toluene 2585 parts. The mixture was stirred in a nitrogen atmosphere while raising the temperature of the contained solution to 50° C. The above-obtained catalyst solution 11.6 parts was added to start the reaction. Next, from the start of the reaction, a solution obtained by dissolving ethylene oxide 129.3 parts in toluene 302 parts was continuously added over 5 hours at an equal speed. Further, every 30 minutes after the start of the reaction, the catalyst solution was added 6.2 parts at a time over 5 hours. Next, water was added in 15 parts and the result stirred to end the reaction. To this, further, an antiaging agent comprised of 4,4'-thiobis-(6-tert-butyl-3-methylphenol) in a 5% toluene solution was added in 45 parts and stirred. This was steam stripped, then the supernatant was removed and the remainder was dried in vacuo at 60° C. to obtain polyether rubber in 400 parts. The monomer composition ratio of this polyether rubber was epichlorohydrin units 40 mol % and ethyleneoxide units 60 mol %. Further, the number average molecular weight was 220,000 (average 3469-mer). Next, to a glass reactor equipped with a stirrer, the obtained polyether rubber 181 parts and toluene 1211 parts were added. These were stirred at 50° C. for 12 hours to make the polyether rubber dissolve. Next, methanol 140 parts were added and the result stirred for 15 minutes. To this, 1-methylimidazole 465 parts were added. The mixture was stirred while raising it to 90° C. and was reacted at 90° C. for 720 hours. After 720 hours, the reaction solution was cooled to 20° C. to stop the reaction. This reaction solution was solidified by distilling off the solvent by steam, then was dried in vacuo to recover hard, solid polyether rubber with chloro groups of the epichlorohydrin units converted to imidazolium in 240 parts. The obtained imidazolium-modified polyether rubber 30 mg was added to 1.0 ml dichloroform and shaken for 1 hour to make it uniformly dissolve. This solution was measured by $^1$H-NMR to calculate the ratio of imidazolium structure-containing units. The ratio of the imidazolium structure-containing units of the obtained imidazolium-modified polyether rubber was 39.8 mol %, while the number average molecular weight was 240,000.

Comparative Production Example 6

Anion Exchange of Imidazolium-Modified Polyether Rubber by Lithium(Bistrifluoromethylsulfone)Imide Except for using, instead of the imidazolium structure-containing polyether compound which has halide ions as counter anions which was obtained at Production Example B, imidazolium-modified polyether rubber which has halide ions as counter anions which was obtained at Comparative Production Example I, in 2.5 g, the same procedure was followed as in Production Example 2, whereupon a colorless, transparent hard rubber solid 4.6 g was obtained. The obtained solid was measured by $^1$H-NMR spectrometry and elemental analysis, whereupon it was identified as an imidazolium-modified polyether rubber wherein all of the chloride ions of the starting material imidazolium-modified polyether rubber which has halide ions as counter anions were exchanged with (bistrifluoromethylsulfone)imide anions.

Example 1

The imidazolium structure-containing polyether compound which has hydroxide ions as counter anions which was obtained at Production Example 1 was aged in an environment of an air temperature of 25° C. and a humidity of 0% for 24 hours. The polyether compound rose somewhat in viscosity to become highly viscous and oily, but was not excessively fluid and could be sufficiently shaped. Next, the aged polyether compound was worked into a diameter 12 mm, thickness 200 micron thin cylindrical shape which was assembled into a coil-shaped cell. The volume specific resistance value was measured, whereupon it was $10^{1.75}$ (Ω/cm). The compositions and properties of the polyether compounds and the values of the volume specific resistance values are shown summarized in Table 1.

TABLE 1

| | Examples | | | | | | | | |
|---|---|---|---|---|---|---|---|---|---|
| | 1 | 2 | 3 | 4 | 5 | 6 | 7 | 8 | 9 |
| Number of repeating units per one molecule (average) | 11 | 11 | 11 | 11 | 11 | 57 | 14 | 16 | 98 |
| Ratio of content of imidazolium structure-containing units (mol %) | 100 | 100 | 100 | 100 | 84.0 | 100 | 71.0 | 50.0 | 85.0 |
| Ratio of content of repeating units represented by general formula (2) (mol %) | 100 | 100 | 100 | 100 | 64.0 | 100 | 71.0 | 50.0 | 85.0 |
| Type of counter anions of imidazolium structure | OH$^-$ | (CF$_2$SO$_2$)$_2$N$^-$ | (FSO$_2$)$_2$N$^-$ | BF$_4^-$ | (CF$_2$SO$_2$)$_2$N$^-$ | (CF$_2$SO$_2$)$_2$N$^-$ | (CF$_2$SO$_2$)$_2$N$^-$ | OH$^-$ | (CF$_2$SO$_2$)$_2$N$^-$ |
| Property after aging | Oily | Oily | Oily | Oily | Oily | Oily | Oily | Oily | Oily |
| Common log of volume specific resistance [Ω/cm] | 1.75 | 2.20 | 2.05 | 1.96 | 2.95 | 2.85 | 3.03 | 3.01 | 3.32 |

| | Comparative Examples | | | | | |
|---|---|---|---|---|---|---|
| | 1 | 2 | 3 | 4 | 5 | 6 |
| Number of repeating units per one molecule (average) | 11 | 11 | 11 | 16 | 1032 | 3469 |
| Ratio of content of imidazolium structure-containing units (mol %) | 0 | 100 | 100 | 50.0 | 100 | 39.8 |
| Ratio of content of repeating units represented by general formula (2) (mol %) | 0 | 0 | 0 | 0 | 100 | 39.8 |
| Type of counter anions of imidazolium structure | None | Cl$^-$ | I$^-$ | Anion of 57 atoms | (CF$_2$SO$_4$)$_4$N$^-$ | (CF$_2$SO$_2$)$_2$N$^-$ |
| Property after aging | Oily | Powdery | Powdery | Soild | Rubbery solid | Hand rubbery solid |

TABLE 1-continued

| Common log of volume specific resistance [Ω/cm] | 8.05 | Not measurable (not shapeable) | Not measurable (not shapeable) | 6.70 | 6.50 | 7.90 |

Examples 2 to 9

Except for using, instead of the polyether compound which was obtained in Production Example 1, the polyether compounds which were obtained in Production Examples 2 to 9, the same procedure was followed as in Example 1 to age the compound and measure the volume specific resistance value. The compositions and properties of the polyether compounds used and the values of the volume specific resistance value are shown together in Table 1.

Comparative Example 1

Except for using, instead of the polyether compound which was obtained in Production Example 1, the oligomer which was comprised by the epichlorohydrin units which were obtained in Production Example A as is, the same procedure was followed as in Example 1 to age the compound and measure the volume specific resistance value. The composition and properties of the oligomer used and the value of the volume specific resistance value are shown together in Table 1.

Comparative Example 2

Except for using, instead of the polyether compound which was obtained in Production Example 1, the imidazolium structure-containing polyether compound which has halide ions as counter anions which was obtained at the Production Example B as is, the same procedure was followed as in Example 1 to age the compound. The polyether compound after aging remained a powder state and did not change. Further, it was attempted to assemble the polyether compound in a coin shaped cell, but it was impossible to work it to a cylindrical shape.

Comparative Examples 3 to 6

Except for using, instead of the polyether compound which is obtained in Production Example 1, the polyether compounds (polyether rubbers) which were obtained in Comparative Production Examples 3 to 6 respectively, the same procedure was followed as in Example 1 to age the compound and measure the volume specific resistance value. The compositions and properties of the polyether compounds used and the values of the volume specific resistance values are shown together in Table 1. Note that, in Comparative Example 3, it was attempted to assemble the polyether compound in a coin shaped cell, but it was impossible to work it to a cylindrical shape.

As will be understood from the results which are shown in Table 1, the polyether compound of the present invention had suitable fluidity and further was excellent in ion conductivity (Examples 1 to 9). On the other hand, the polyether compound which does not contain repeating units which are represented by the general formula (2) did not have suitable fluidity and was inherently difficult to shape (Comparative Examples 2 and 3) and was inferior in ion conductivity (Comparative Examples 1 and 4). Further, the polyether compound which contains the repeating units which are represented by the general formula (2) which has too many repeating units forming the polyether compound did not have suitable fluidity and was inferior in ion conductivity (Comparative Examples 5 and 6).

The invention claimed is:

1. A polyether compound containing repeating units which are represented by the following general formula (1) in an average number per molecule of 10 to 100, which contains as at least part of the repeating units which are represented by the general formula (1), one or more units which are represented by the following general formula (2), wherein a number average molecular weight of the polyether compound is 1,000 to 50,000

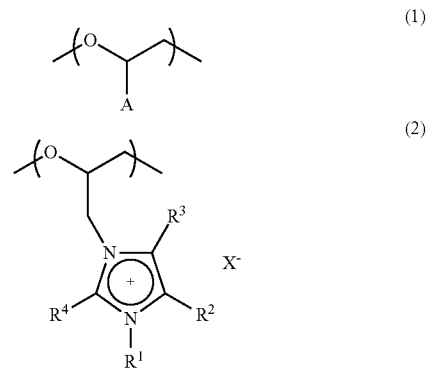

wherein in the general formula (1), A is a monovalent group; and in the general formula (2), $R^1$ to $R^4$ respectively independently are a hydrogen atom or a $C_1$ to $C_3$ alkyl group, and $R^2$ and $R^3$ may be bonded with each other; and $X^-$ is an anion which is comprised of 2 to 25 atoms.

2. The polyether compound as set forth in claim 1, wherein in the general formula (2), the anion which is represented by $X^-$ and is comprised of 2 to 25 atoms is any of $OH^-$, $SCN^-$, $BF_4^-$, $PF_6^-$, $ClO_4^-$, $(FSO_2)_2N^-$, $(CF_3SO_2)_2N^-$, $(CF_3CF_2SO_2)_2N^-$, $CH_3SO_3^-$, $CF_3SO_3^-$, $CF_3COO^-$, or $PhCOO^-$.

3. The polyether compound as set forth in claim 1, wherein, in the repeating units which are expressed by the general formula (1), the ratio of the one or more units which are represented by the general formula (2) is 2 mol % or more.

4. The polyether compound as set forth in claim 1, wherein, in the repeating units which are represented by the general formula (1), one or more units other than the one or more units which are represented by the general formula (2) include one or more units selected from units where the monovalent group which is represented by A in the general formula (1) is a hydrogen atom, units where it is an alkyl group, and units where it is a haloalkyl group, and units which have the same structure as the units which are represented by the general formula (2) except anions where $X^-$ is comprised of a single atom.

5. An electrolyte composition which contains the polyether compound as set forth in claim 1.

6. A method of production of the polyether compound as set forth in claim 1 comprising, a step of ring opening polymerizing a monomer composition which contains epichlorohydrin in the presence of an onium salt of a compound which contains atoms of Group XV or Group XVI of the Periodic Table and trialkyl aluminum where all of the contained alkyl groups are linear alkyl groups so as to obtain an epichlorohydrin unit-containing polyether compound, a step of reacting the obtained epichlorohydrin unit-containing polyether compound with an imidazole compound so as to obtain an imidazolium chloride structure unit-containing polyether compound, and a step of reacting the obtained imidazolium chloride structure unit-containing polyether compound with a salt of an anion comprised of 2 to 25 atoms and a metal cation to perform an anion exchange reaction.

* * * * *